United States Patent
Tuschel et al.

(10) Patent No.: US 7,701,572 B2
(45) Date of Patent: Apr. 20, 2010

(54) SYSTEM AND METHOD FOR CHEMICAL IMAGING OF MICROARRAYS

(75) Inventors: David Tuschel, Monroeville, PA (US); Thomas C. Voigt, Export, PA (US)

(73) Assignee: ChemImage Corporation, Pittsburgh, PA (US)

( * ) Notice: Subject to any disclaimer, the term of this patent is extended or adjusted under 35 U.S.C. 154(b) by 148 days.

(21) Appl. No.: 11/918,487

(22) PCT Filed: Apr. 8, 2005

(86) PCT No.: PCT/US2005/011922

§ 371 (c)(1),
(2), (4) Date: Oct. 15, 2007

(87) PCT Pub. No.: WO2006/110135

PCT Pub. Date: Oct. 19, 2006

(65) Prior Publication Data

US 2009/0059220 A1 Mar. 5, 2009

(51) Int. Cl.
*G01N 21/64* (2006.01)
*G01N 21/65* (2006.01)
*G01J 3/51* (2006.01)
*G01J 3/44* (2006.01)

(52) U.S. Cl. .................. 356/301; 356/417; 356/418

(58) Field of Classification Search .................. 356/73, 356/301, 417, 418
See application file for complete search history.

(56) References Cited

U.S. PATENT DOCUMENTS

| 5,854,684 | A | * | 12/1998 | Stabile et al. ............... 356/440 |
|---|---|---|---|---|
| 5,986,271 | A | * | 11/1999 | Lazarev et al. ........... 250/458.1 |
| 6,191,852 | B1 | | 2/2001 | Paffhausen et al. |
| 6,665,072 | B2 | | 12/2003 | Hoyt |
| 2002/0135770 | A1 | * | 9/2002 | Lewis et al. ................. 356/419 |

* cited by examiner

*Primary Examiner*—F. L Evans
(74) *Attorney, Agent, or Firm*—Duane Morris LLP

(57) ABSTRACT

The disclosure relates to systems and method for chemical imaging of microarrays. In one embodiment, the disclosure relates to a system for simultaneous spectral imaging of a plurality of samples arranged on an array. The system includes an illumination source for providing illuminating photons to said plurality of samples, the illuminating photons interacting with each of the plurality of samples to emit interacted photons; an array for receiving said plurality of samples, the array having an external dimension such that the samples are within a simultaneous field of view of the optical device; an optical device for collecting the interacted photons and directing the photons to an imaging device, the imaging device simultaneously forming a plurality of images corresponding to each of the plurality of samples.

31 Claims, 2 Drawing Sheets

SYSTEM AND METHOD FOR CHEMICAL
IMAGING OF MICROARRAYS

BACKGROUND

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e., chemical) imaging typically comprise image gathering optics, focal plane array imaging detectors and imaging spectrometers.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscopes or rigid borescopes can be employed. For very large scale objects, such as planetary objects, telescopes are appropriate image gathering optics.

Often the array under study includes multiple samples arranged on an array card. Conventional arrays include 4 in×6 in well plates having typically 96 wells for receiving samples. The samples in each well can include similar or dissimilar substances. Thus, for example, a conventional array can include as many as 96 different samples. To obtain a spectral image or spectra(um) for each sample with a conventional micro-Raman instrument an excitation in the form of a spot laser beam of desired wavelength ($\lambda_{illum}$) is directed to one of the 96 samples. After a suitable image or spectra(um) of the first sample is procured, the illumination source is directed to the subsequent well and the process is repeated. The conventional method of serially imaging each sample is time-consuming and labor intensive.

SUMMARY

In one embodiment, the disclosure relates to a method for simultaneously obtaining a spectral image of plural samples of an array. Each image is spatially resolved. In one embodiment, the method may include (a) simultaneously illuminating each of the plurality of samples with illuminating photons, said illuminating photons interacting with each sample to produce interacted photons from each sample; (b) collecting the interacted photons from each sample simultaneously; and (c) forming a spectral image from the collected photons for each of the plurality of sample simultaneously.

In another embodiment, the disclosure relates to a method for simultaneous spectroscopic imaging of samples. The method includes providing an array defined by at least two samples, illuminating each of the two samples with illuminating photons, said illuminating photons interacting with each sample to produce interacted photons from each sample; collecting the interacted photons from each sample simultaneously with an optical device; and forming a spectral image from the collected photons for each sample simultaneously with a processing apparatus. In one embodiment, the array has an external dimension such that the samples are within a simultaneous field of view of the optical device.

In still another embodiment, the disclosure relates to a system for simultaneous spectral imaging of a plurality of samples arranged on an array. The system includes an illumination source for providing illuminating photons to said plurality of samples, the illuminating photons interacting with each of the plurality of samples to emit interacted photons; an array for receiving said plurality of samples, the array having an external dimension such that the samples are within a simultaneous field of view of the optical device; an optical device for collecting the interacted photons and directing the photons to an imaging device, the imaging device simultaneously forming a plurality of images corresponding to each of the plurality of samples. Each image is spatially resolved.

DETAILED DESCRIPTION

Figure 1:
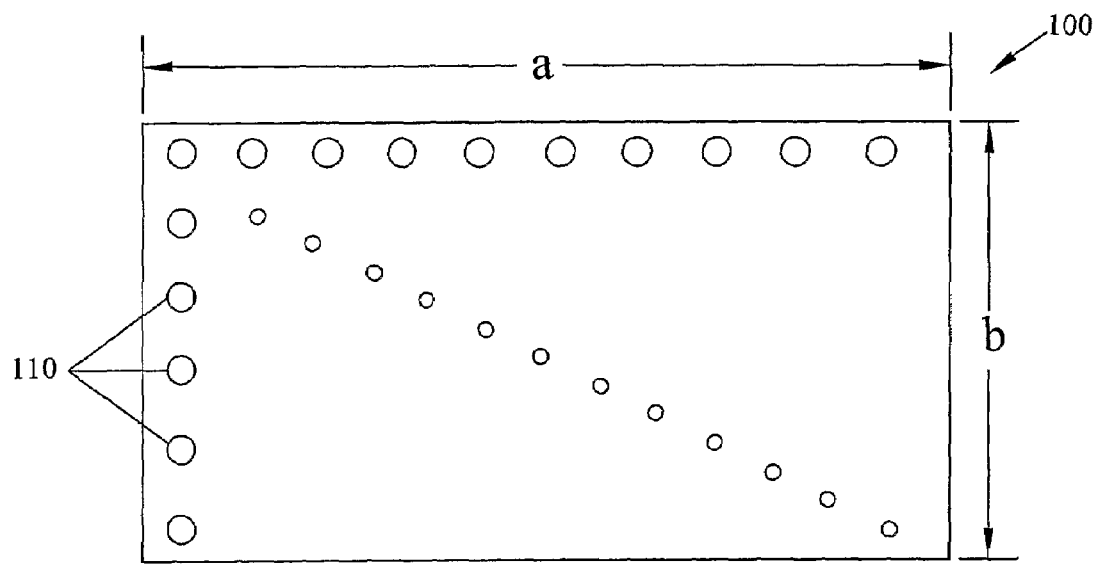
FIG. 1 is a schematic representation of a conventional array having multiple sample wells.

FIG. 1 is a schematic representation of a conventional array having multiple sample wells. Specifically, FIG. 1 shows array card 100 having wells 110. Wells 110 are adapted to each receive a sample (not shown). The sample can be a biological sample, an organic sample or an inorganic sample. Array 100 can be seen as having a dimensions of a×b. A typical array card has a dimensions of 3 in×4 in with a total of 96 wells. The size of the array card makes it improbable, if not impossible, to fit all of the samples in each well (e.g., 96 samples) within the field of view of the imaging device. In other words, the field of view of the imaging device is too small to allow simultaneous spectral imaging of more than one sample at a time. Consequently, each sample must be imaged individually.

Figure 2:
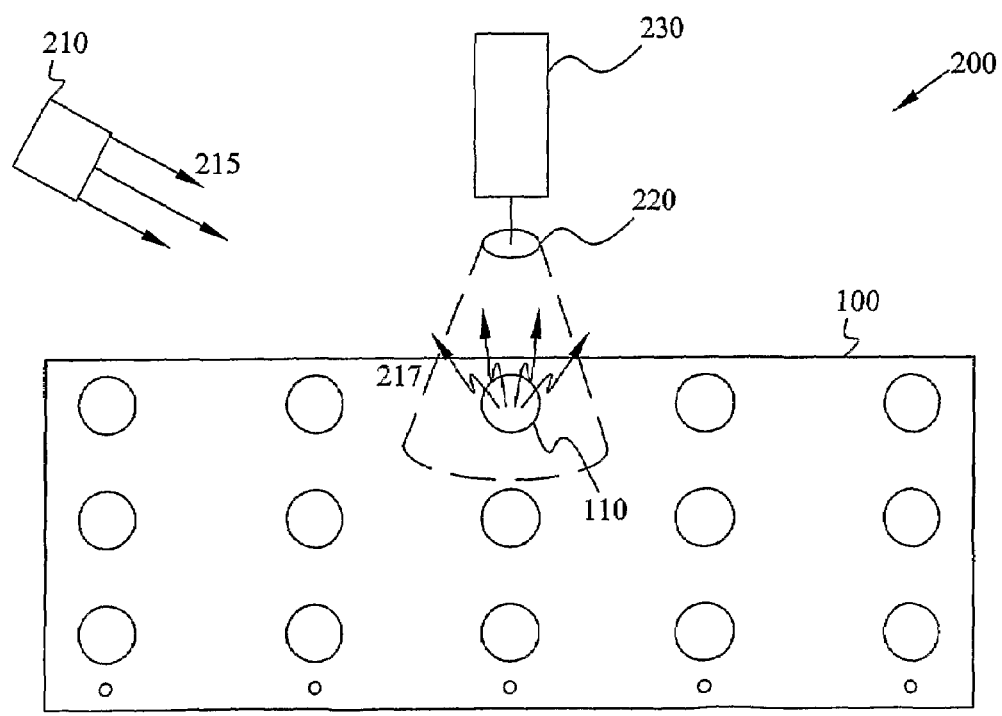
FIG. 2 is a schematic representation of a system for spectral imaging of the samples in the array of FIG. 1.

FIG. 2 is a schematic representation of a system for spectral imaging of the samples in the array of FIG. 1. System 200 includes array card 100 having wells 110 with each well containing a sample. Illumination source 210 directs illuminating photons 215 having illuminating wavelength ($\lambda_{illum}$) to a targeted sample contained in well 110. The illuminating photons interact with the sample and emit interacted photons 217 from the target well. To form an image from emitted photons 217, the target well must be within the field of view of optical device 220. Optical device 220 gathers and directs interacted photons to imaging system 203 which forms an image of the sample contained in target well 110.

Because of diffraction limitations of the optical device 220 and the size of array 100, the field of view of the entire system is limited to one sample and any image of the multiple samples will not be spatially resolved. It can be readily seen from the schematic representation of FIG. 2, that optical device 220 is limited to the field of view of the well immediately before it. Consequently, the wells have to be sampled one at a time in serial fashion. To this end, the operator must move array 100 in X and/or Y directions sequentially to obtain a spectral image of one sample at-a-time.

According to one embodiment of the disclosure, the shape, size or form of array 100 is configured such that all of the samples fall within the field of view of the optical gathering device. For example, a system according to one embodiment of the disclosure includes an illumination source for providing illuminating photons to said plurality of samples. The illumination can be positioned above, below or in an oblique angle with respect to the array. The illuminating photons interact with each of the plurality of samples, substantially simultaneously, to emit interacted photons. An optical device then collects interacted photons and directs the photons to an imaging device for simultaneously forming a plurality of images corresponding to each of the plurality of samples.

An array according to one embodiment of the disclosure can have external dimensions such that all or a number of the samples fall within the field of view of the optical device or the gathering optics. Because the field of view of a gathering optic is a function of the optic's diffraction capability as well as its distance from the sample, the array dimensions can be adapted to enable substantially all of the samples to be within the field of view of the gathering optics. Thus, according to one embodiment, the dimensions of the array are defined as a function of the distance between the array and the optics' focal point. According to another embodiment, the dimensions of the array are defined such that a portion or all of the samples fall within the field of view of the gathering optics. Thus, a spectral image of all of the samples can be formed simultaneously without having to move the array.

Figure 3:
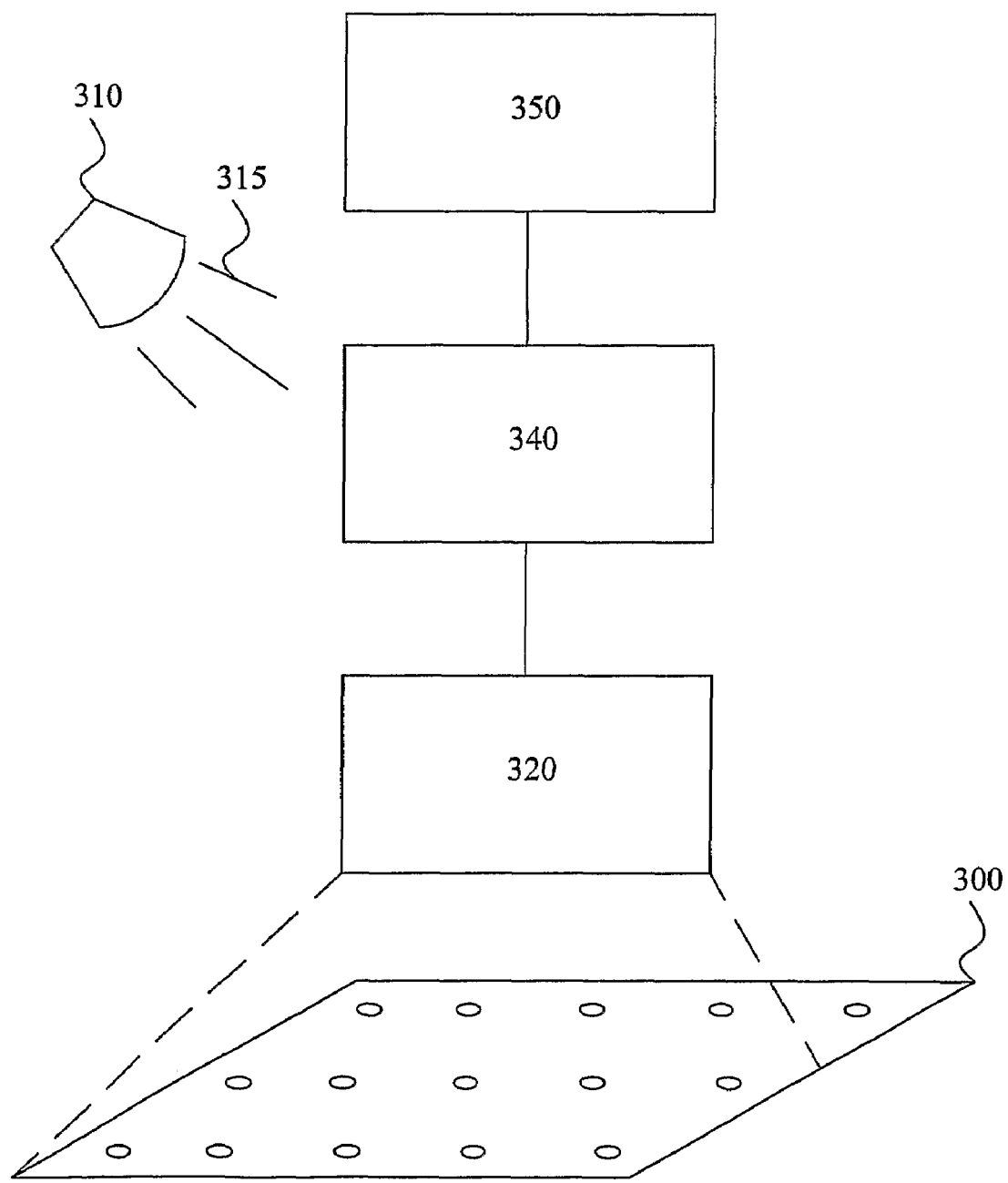
FIG. 3 is a schematic drawing of an array according to one embodiment of the disclosure.

FIG. 3 is a schematic drawing of an array according to one embodiment of the disclosure. Specifically, array 300 is shown with respect to an imaging system for capturing multiple images of the samples simultaneously. The samples are arranged on array card 300 and the array card 300 is sized such that all of the samples fall within the field of view of gathering optics 320. Gathering optics 320 can include, for example, one or more of objective lenses and optical filters.

Illumination source 310 can be any suitable emission source adapted to produce photons having the desired excitation wavelength. While illumination source 310 is positioned at an oblique angle with respect to array 300, the disclosure is not limited thereto. For example, illumination source 310 can be positioned below array 300 or above array 300 concentric with gathering optics 320 such that excitation photons 315 can reach well 300.

Gathering optics 320 simultaneously collects all, or nearly all of interacted photons emitted by the samples. The interacted photons may include Raman, Fluorescence, absorption, reflection and transmitted photons. The interacted photons can be formed by the interaction of illuminating photons with each sample. Gathering optics 320 focuses the collected photons (not shown) and directs an image formed therefrom to tunable filter 340. Tunable filter 340 may include a liquid crystal tunable filter ("LCTF"), a filter wheel or an acousto-optical tunable filter. Tunable filter 340 can generate a plurality of spectra (filtered wavelengths) corresponding to each of the samples in array 300. An image forming device such as a charge-coupled device ("CCD") or a CMOS image sensor can receive filtered wavelengths from tunable filter 340 and simultaneously form an image from multiple wells. Since several, if not all, of the samples are within the field of view of gathering optics 320, the images formed by device 350 includes an image for each of the corresponding samples in the array.

According to one embodiment of the disclosure, a method for simultaneously obtaining spectral images of a plurality of samples in an array includes: (a) simultaneously illuminating each of the plurality of samples with illuminating photons to produce interacted photons from each of the samples; (b) collecting the interacted photons from each sample simultaneously; and (c) forming a spectral image from the collected photons for all samples simultaneously. The interacted photons can include Raman, Absorption, fluorescence and reflection photons.

In still another embodiment, the array is designed to have outside dimensions of about 1-100 mm², for example, 3 mm², 4 mm², 6 mm², 10 mm². Other exemplary dimensions include 2×4 mm², 4×4 mm², 6×4 mm² and 6×8 mm². The dimensions and the positions of the wells can be adapted to accommodate the outside dimensions of the array. Moreover, the number of wells can be increased or decreased depending on the desired application. The array dimensions provided herein are exemplary in nature. Other array dimensions not specifically disclosed are deemed within the scope of the principles disclosed herein.

In another embodiment a magnification lens, or other optical device, can be interposed between array 300 and optical device 320 to optically reduce the size of the array card such that multiples samples can fit in the view of optical device 320. The magnification lens can be a stand-alone peripheral unit or can be combined with gathering optics 320.

While the principles of the disclosure have been disclosed in relation to specific exemplary embodiments, it is noted that the principles of the invention are not limited thereto and include all modification and variation to the specific embodiments disclosed herein.

What is claimed is:

1. In a method for providing spectral image of an array of samples provided on a substrate by illuminating each sample independently of other samples, the improvement comprising the steps of: (i) illuminating all samples with photons simultaneously to produce emitted photons from each sample; (ii) simultaneously receiving emitted photons from all samples at a tunable filter; and; (iii) forming a spectral image from the emitted photons, the spectral image including a plurality of sub-images, each sub-image corresponding to a sample in the array of samples.

2. The method of claim 1, wherein the emitted photons further comprise Raman, absorption, fluorescence, reflection and transmitted photons.

3. The method of claim 1, wherein the tunable falter is selected from the group consisting of LCTF and AOTF.

4. The method of claim 1, further comprising the step of: (iv) selecting a sub-image from the plurality of sub-images; and (v) forming an independent image of said sample.

5. A method for simultaneously obtaining a spectral image of plural samples of an array, comprising: (a) simultaneously illuminating each of the plurality of samples with illuminating photons, said illuminating photons interacting with each sample to produce interacted photons from each sample; (b) collecting the interacted photons from each sample simultaneously; and (c) forming a spectral image from the collected photons for each of the plurality of samples simultaneously.

6. The method of claim 5, filtering detected photons through a tunable filter.

7. The method of claim 5, wherein interacted photons include Raman, Absorption, fluorescence and reflection.

8. The method of claim 5, further comprising providing an array having a plurality of wells.

9. The method of claim 5, further comprising providing an array defined by a substrate having a plurality of samples.

10. The method of claim 5, further comprising providing an array defined by a substrate having a plurality of samples, said array having a dimension not larger than 6 mm².

11. The method of claim 5, further comprising providing an array defined by a substrate having a plurality of samples, said array having a dimension not larger than 3 mm².

12. The method of claim 5, wherein the spectral image of the plurality of samples is spatially-resolved.

13. A method for simultaneous spectroscopical imaging of samples comprising: providing an array defined by at least two samples, illuminating each of the two samples with illuminating photons, said illuminating photons interacting with each sample to produce interacted photons from each sample; collecting the interacted photons from each sample simultaneously with an optical device; and forming a spectral image from the collected photons for each sample simultaneously with a processing apparatus; wherein the array has an external dimension such that the samples are within a simultaneous field of view of the optical device.

14. The method of claim 13, wherein illuminating each of the two samples is simultaneous.

15. The method of claim 13, wherein the processing apparatus is a tunable filter.

16. The method of claim 13, wherein the optical device further comprises an optical lens.

17. The method of claim 13, filtering detected photons through a tunable filter.

18. The method of claim 13, wherein interacted photons include Raman, Absorption, fluorescence and reflection.

19. The method of claim 13, further comprising providing an array having a plurality of wells.

20. The method of claim 13, wherein the array is not larger than 6 mm$^2$.

21. The method of claim 13, wherein the array is not larger than 3 mm$^2$.

22. A system for simultaneous spectral imaging of a plurality of samples arranged on an array, comprising:
   an illumination source for providing illuminating photons to said plurality of samples, the illuminating photons interacting with each of the plurality of samples to emit interacted photons;
   an optical device for collecting the interacted photons and directing the photons to an imaging device, the imaging device simultaneously forming a plurality of images corresponding to each of the plurality of samples; wherein each of the plurality of samples is spatially-resolved; and
   an array for receiving said plurality of samples, the array having an external dimension such that the samples are within a simultaneous field of view of said optical device.

23. The system of claim 22, wherein the spectral imaging further comprises Raman imaging and Fluorescent imaging.

24. The system of claim 23, wherein the interacted photons include Raman, fluorescence, illuminating, emitted reflection, absorption and transmission photons.

25. The system of claim 22, wherein the illumination source is a laser light source.

26. The system of claim 22, wherein the illumination source is a spot-laser.

27. The system of claim 22, wherein the optical device further comprises a lens.

28. The system of claim 22, wherein the optical device further comprises an optical filter.

29. The system of claim 22, wherein the imaging device further comprises a tunable filter and a charge-coupled device.

30. The system of claim 22, wherein the array further comprises a substrate having a dimension of less than 1 cm$^2$.

31. The system of claim 22, wherein the array further comprises a substrate having a dimension of less than 3 mm×4 mm.

* * * * *